US007288080B2

(12) United States Patent
Edens et al.

(10) Patent No.: US 7,288,080 B2
(45) Date of Patent: Oct. 30, 2007

(54) LABIAL PAD

(75) Inventors: Ronald L. Edens, Cumming, GA (US); James J. Hlaban, Neenah, WI (US); Laura J. Keely, Neenah, WI (US); Thomas P. Keenan, Appleton, WI (US); Sylvia B. Little, Marietta, GA (US); Mary L. McDaniel, Appleton, WI (US); Stephen L. Nunn, Appleton, WI (US); William G. Reeves, Appleton, WI (US); Heather A. Sorebo, Appleton, WI (US); Susan M. Weyenberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1024 days.

(21) Appl. No.: 10/037,276

(22) Filed: Dec. 31, 2001

(65) Prior Publication Data

US 2002/0193770 A1  Dec. 19, 2002

Related U.S. Application Data

(60) Provisional application No. 60/297,002, filed on Jun. 8, 2001.

(51) Int. Cl.
*A61F 13/15* (2006.01)
*A61F 13/20* (2006.01)
(52) U.S. Cl. .......................... 604/385.17; 604/385.18; 604/904
(58) Field of Classification Search ........... 604/385.17, 604/385.18, 904
See application file for complete search history.

(56) References Cited

U.S. PATENT DOCUMENTS

| 271,625 | A | 2/1883 | Goff |
|---|---|---|---|
| 2,092,346 | A | 9/1937 | Arone |
| 2,123,750 | A | 7/1938 | Schulz |
| 2,328,795 | A | 9/1943 | Finks |
| 2,331,355 | A | 10/1943 | Strongson |
| 2,408,508 | A | 10/1946 | Canavan |
| 2,629,381 | A | 2/1953 | Brown |
| 2,662,527 | A | 12/1953 | Jacks |
| 2,676,594 | A | 4/1954 | Milcent |
| 2,682,875 | A | 7/1954 | Brown |
| 2,771,882 | A | 11/1956 | Leupold |
| 2,917,049 | A | 12/1959 | Delaney |

(Continued)

FOREIGN PATENT DOCUMENTS

CA          2277728          11/1999

(Continued)

OTHER PUBLICATIONS

English abstract of JP 2000-511078 T2: Description of R. L. Buck et al., "Method and apparatus for collecting vaginal fluid and exfoliated vaginal cells for diagnostic purposes.".

(Continued)

*Primary Examiner*—Michele Kidwell
(74) *Attorney, Agent, or Firm*—Sebastian C. Pugliese, III

(57) ABSTRACT

An absorbent article (40), such as a labial pad, configured for disposition within the vestibule (42) of a female wearer. The absorbent article (40) may be worn by females for catamenial purposes, incontinence protection, or both.

32 Claims, 10 Drawing Sheets

U.S. PATENT DOCUMENTS

| | | |
|---|---|---|
| 3,097,648 A | 7/1963 | Dupuis |
| 3,183,909 A | 5/1965 | Roehr |
| 3,406,689 A | 10/1968 | Hicks et al. |
| 3,411,504 A | 11/1968 | Glassman |
| 3,420,234 A | 1/1969 | Phelps |
| 3,420,235 A | 1/1969 | Harmon |
| 3,528,422 A | 9/1970 | Hodas |
| 3,575,174 A | 4/1971 | Mogor |
| 3,690,321 A | 9/1972 | Hirschman |
| 3,726,277 A | 4/1973 | Hirschman |
| 3,736,931 A | 6/1973 | Glassman |
| 3,857,394 A | 12/1974 | Alemany |
| 3,905,372 A | 9/1975 | Denkinger |
| 3,983,873 A | 10/1976 | Hirschman |
| 3,993,074 A | 11/1976 | Murray et al. |
| 4,046,147 A | 9/1977 | Berg |
| 4,067,336 A | 1/1978 | Johnson |
| D247,368 S | 2/1978 | Whitehead |
| 4,079,739 A | 3/1978 | Whitehead |
| 4,095,542 A | 6/1978 | Hirschman |
| 4,142,476 A | 3/1979 | Hirschman |
| 4,166,464 A | 9/1979 | Korpman |
| 4,175,561 A | 11/1979 | Hirschman |
| 4,182,334 A | 1/1980 | Johnson |
| 4,184,498 A | 1/1980 | Franco |
| 4,196,562 A | 4/1980 | Hirschman |
| 4,212,301 A | 7/1980 | Johnson |
| 4,315,507 A | 2/1982 | Whitehead et al. |
| 4,340,058 A | 7/1982 | Pierce et al. |
| D266,873 S | 11/1982 | Riedell |
| D272,188 S | 1/1984 | Sneider |
| D276,554 S | 11/1984 | Glassman |
| 4,490,147 A | 12/1984 | Pierce et al. |
| 4,533,357 A | 8/1985 | Hall |
| 4,548,603 A | 10/1985 | Ichijo |
| 4,589,876 A | 5/1986 | Van Tilburg |
| 4,595,392 A | 6/1986 | Johnson et al. |
| 4,605,404 A | 8/1986 | Sneider |
| 4,623,341 A | 11/1986 | Roeder |
| 4,624,666 A | 11/1986 | DeRossett et al. |
| 4,627,848 A | 12/1986 | Lassen et al. |
| 4,631,062 A | 12/1986 | Lassen et al. |
| 4,673,403 A | 6/1987 | Lassen et al. |
| 4,678,464 A | 7/1987 | Holtman |
| 4,685,914 A | 8/1987 | Holtman |
| 4,687,478 A | 8/1987 | Van Tilburg |
| 4,690,680 A | 9/1987 | Higgins |
| D292,611 S | 11/1987 | Titus |
| 4,743,245 A | 5/1988 | Lassen et al. |
| 4,773,905 A | 9/1988 | Molee et al. |
| 4,781,713 A | 11/1988 | Welch et al. |
| 4,804,380 A * | 2/1989 | Lassen et al. .......... 604/385.17 |
| D300,658 S | 4/1989 | Sneider |
| 4,820,295 A | 4/1989 | Chapas et al. |
| 4,846,824 A | 7/1989 | Lassen et al. |
| 4,898,642 A | 2/1990 | Moore et al. |
| 4,900,320 A | 2/1990 | McCoy |
| 4,917,697 A | 4/1990 | Osborn, III et al. |
| 4,938,515 A | 7/1990 | Fazio |
| 4,995,150 A | 2/1991 | Gerstenberger et al. |
| 5,057,096 A | 10/1991 | Faglione |
| 5,074,855 A | 12/1991 | Rosenbluth et al. |
| 5,087,254 A | 2/1992 | Davis et al. |
| 5,127,911 A | 7/1992 | Baharav |
| 5,197,959 A | 3/1993 | Buell |
| D342,785 S | 12/1993 | Farrell |
| 5,267,992 A | 12/1993 | Van Tilburg |
| 5,290,262 A | 3/1994 | Vukos et al. |
| 5,320,531 A | 6/1994 | Delizo-Madamba |
| 5,336,208 A | 8/1994 | Rosenbluth et al. |
| 5,383,868 A | 1/1995 | Hyun |
| 5,389,181 A | 2/1995 | Vukos et al. |
| 5,429,630 A | 7/1995 | Beal et al. |
| 5,484,429 A * | 1/1996 | Vukos et al. .......... 604/385.23 |
| 5,509,914 A | 4/1996 | Osborn |
| 5,520,675 A | 5/1996 | Knox-Sigh |
| 5,573,523 A | 11/1996 | Whalen et al. |
| 5,607,414 A | 3/1997 | Richards et al. |
| 5,618,282 A | 4/1997 | Schlangen |
| 5,624,421 A | 4/1997 | Dabi et al. |
| 5,672,165 A | 9/1997 | Belecky et al. |
| 5,676,652 A | 10/1997 | Hunter et al. |
| 5,695,484 A | 12/1997 | Cox |
| 5,713,886 A | 2/1998 | Sturino |
| 5,725,481 A | 3/1998 | Buck et al. |
| 5,738,212 A | 4/1998 | Pollard et al. |
| 5,762,644 A | 6/1998 | Osborn, III et al. |
| 5,795,344 A * | 8/1998 | Chappell .................. 604/379 |
| 5,827,256 A | 10/1998 | Balzar |
| 5,833,680 A | 11/1998 | Hartman |
| 5,849,003 A | 12/1998 | Olsen et al. |
| D404,814 S | 1/1999 | Mayer |
| 5,873,869 A | 2/1999 | Hammons et al. |
| 5,882,743 A | 3/1999 | McConnell |
| 5,885,265 A | 3/1999 | Osborn, III et al. |
| 5,891,123 A | 4/1999 | Balzar |
| 5,891,126 A | 4/1999 | Osborn, III et al. |
| 5,895,381 A | 4/1999 | Osborn, III |
| 5,916,205 A | 6/1999 | Olson et al. |
| 5,928,452 A | 7/1999 | McFall et al. |
| D413,669 S | 9/1999 | Olson et al. |
| 5,951,537 A | 9/1999 | Osborn, III |
| 5,964,689 A | 10/1999 | McFall et al. |
| 5,968,026 A | 10/1999 | Osborn, III et al. |
| 5,987,645 A | 11/1999 | Teaster |
| 6,004,893 A | 12/1999 | Van Tilburg |
| 6,007,498 A | 12/1999 | Buck et al. |
| 6,007,528 A | 12/1999 | Osborn, III |
| 6,010,001 A | 1/2000 | Osborn, III |
| 6,033,391 A | 3/2000 | Osborn, III et al. |
| 6,045,544 A | 4/2000 | Hershberger et al. |
| 6,123,693 A | 9/2000 | Osborn, III |
| 6,131,736 A | 10/2000 | Farris et al. |
| 6,152,905 A | 11/2000 | Osborn, III et al. |
| 6,171,292 B1 | 1/2001 | Osborn, III et al. |
| 6,174,293 B1 | 1/2001 | Buck et al. |
| 6,183,456 B1 | 2/2001 | Brown et al. |
| D439,331 S | 3/2001 | Mitchell |
| 6,203,512 B1 | 3/2001 | Farris et al. |
| 6,214,362 B1 | 4/2001 | Page |
| 6,254,584 B1 | 7/2001 | Osborn, III et al. |
| 6,258,074 B1 | 7/2001 | Prazak |
| 6,261,277 B1 | 7/2001 | Osborn, III et al. |
| 6,270,486 B1 | 8/2001 | Brown et al. |
| 6,319,238 B1 | 11/2001 | Sartorio et al. |
| 6,395,956 B1 * | 5/2002 | Glasgow et al. ............ 604/378 |
| 6,409,714 B2 | 6/2002 | Osborn, III et al. |
| 6,432,096 B1 * | 8/2002 | McFall et al. ......... 604/385.17 |
| 6,475,203 B1 | 11/2002 | Rubio |
| 6,524,290 B2 | 2/2003 | Motta et al. |
| 6,554,813 B2 | 4/2003 | Kolby-Falk |
| 6,613,031 B2 | 9/2003 | Glasgow et al. |
| 2002/0026678 A1 | 3/2002 | Gustafsson et al. |
| 2002/0026679 A1 | 3/2002 | Widlund |
| 2002/0115976 A1* | 8/2002 | Fleming ................ 604/385.17 |
| 2002/0188269 A1 | 12/2002 | Edens et al. |
| 2002/0188270 A1 | 12/2002 | Edens et al. |
| 2002/0188271 A1 | 12/2002 | Kathumbi-Jackson et al. |
| 2002/0188272 A1 | 12/2002 | Hlaban et al. |
| 2002/0193769 A1 | 12/2002 | Edens et al. |
| 2002/0193771 A1 | 12/2002 | Edens et al. |
| 2002/0193772 A1 | 12/2002 | Edens et al. |
| 2002/0193773 A1 | 12/2002 | Edens et al. |
| 2003/0093054 A1 | 5/2003 | Sierri et al. |

| | | | |
|---|---|---|---|
| 2003/0208178 A1 | 11/2003 | Edens et al. | |

FOREIGN PATENT DOCUMENTS

| | | |
|---|---|---|
| CH | 204076 | 4/1939 |
| DE | 40 32 119 A1 | 4/1992 |
| EP | FR 595.971 | 10/1925 |
| EP | FR 2 420 339 | 10/1979 |
| EP | 0 162 451 B1 | 8/1991 |
| EP | 0 302 523 B1 | 4/1994 |
| EP | 0 597 498 A1 | 5/1994 |
| EP | 0 613 671 A2 | 9/1994 |
| EP | 0 426 197 B1 | 10/1997 |
| EP | 0 888 762 A1 | 1/1999 |
| EP | 0 888 763 A1 | 1/1999 |
| EP | 0 680 739 B1 | 3/1999 |
| EP | 1 051 956 A1 | 11/2000 |
| EP | 1 066 810 A2 | 1/2001 |
| EP | 1 072 244 A2 | 1/2001 |
| EP | 0 607 985 B2 | 5/2001 |
| EP | 1 097 683 A2 | 5/2001 |
| GB | 588689 | 5/1947 |
| GB | 754481 | 8/1956 |
| GB | 855537 | 12/1960 |
| GB | 2 214 085 A | 8/1989 |
| GB | 2 227 666 A | 8/1990 |
| GB | 2 238 286 A | 5/1991 |
| GB | 2 259 451 A | 3/1993 |
| GB | 2 306 888 A | 5/1997 |
| JP | 09-99009 A | 4/1997 |
| WO | WO 95/00097 A1 | 1/1995 |
| WO | WO 96/16626 A1 | 6/1996 |
| WO | WO 97/39713 A1 | 10/1997 |
| WO | WO 97/43955 A1 | 11/1997 |
| WO | WO 98/00085 A1 | 1/1998 |
| WO | WO 98/08475 A1 | 3/1998 |
| WO | WO 98/13002 A1 | 4/1998 |
| WO | WO 98/29075 A1 | 7/1998 |
| WO | WO 98/29077 A1 | 7/1998 |
| WO | WO 98/29078 A1 | 7/1998 |
| WO | WO 98/51249 A1 | 11/1998 |
| WO | WO 98/55158 A1 | 12/1998 |
| WO | WO 98/55159 A2 | 12/1998 |
| WO | WO 98/57608 A1 | 12/1998 |
| WO | WO 98/57609 A1 | 12/1998 |
| WO | WO 98/57610 A1 | 12/1998 |
| WO | WO 99/00083 A1 | 1/1999 |
| WO | WO 99/01095 A1 | 1/1999 |
| WO | WO 99/18905 A1 | 4/1999 |
| WO | WO 99/25289 A1 | 5/1999 |
| WO | WO 99/25295 A1 | 5/1999 |
| WO | WO 99/26573 A1 | 6/1999 |
| WO | WO 99/26574 A1 | 6/1999 |
| WO | WO 99/26575 A1 | 6/1999 |
| WO | WO 99/26576 A1 | 6/1999 |
| WO | WO 99/26577 A1 | 6/1999 |
| WO | WO 99/26578 A1 | 6/1999 |
| WO | WO 99/26770 A1 | 6/1999 |
| WO | WO 99/55272 A1 | 11/1999 |
| WO | WO 99/56681 A2 | 11/1999 |
| WO | WO 99/56689 A1 | 11/1999 |
| WO | WO 00/40197 A1 | 7/2000 |
| WO | WO 00/65348 A2 | 11/2000 |
| WO | WO 00/69481 A1 | 11/2000 |
| WO | WO 00/69482 A1 | 11/2000 |
| WO | WO 00/69484 A1 | 11/2000 |
| WO | WO 00/69485 A1 | 11/2000 |
| WO | WO 00/72790 A1 | 12/2000 |
| WO | WO 01/00128 A1 | 1/2001 |
| WO | WO 01/35887 A1 | 5/2001 |
| WO | WO 01/45610 A1 | 6/2001 |
| WO | WO 01/60297 A1 | 8/2001 |

OTHER PUBLICATIONS

Gray, Henry, Anatomy of the Human Body, vol. II, Thirtieth American Edition, published by Lea and Febiger, 1985, pp. 1566-1586.

* cited by examiner

LABIAL PAD

This application claims priority from U.S. Provisional Application No. 60/297,002 filed on Jun. 8, 2001.

BACKGROUND

The present invention relates generally to absorbent articles. More particularly, the present invention relates to absorbent articles such as labial pads configured for disposition within the vestibule of a female wearer.

A broad manner and wide variety of absorbent articles configured for the absorption of bodily exudates such as menstrual fluid are, of course, well known. With respect to feminine hygiene, the art has offered two basic types of feminine hygiene protection: sanitary napkins, developed for external wear about the pudendal region, and tampons, developed for residence within the vaginal cavity and interruption of menstrual flow therefrom. Hybrid feminine hygiene protection devices, attempting to merge the structural features of both within a single type of device, have also been proposed, but have not seen a meaningful measure of acceptance insofar as the effort to appropriate advantages has been overshadowed by the more demonstrable perpetuation of structural and anatomically functional disadvantages. Other less intrusive devices, known as labial or interlabial devices and characterized as having a portion which at least partially resides external of the wearer's vestibule, have also been proposed.

Many of these prior devices have not fully satisfied the demand of consumers for even smaller devices that may be worn interlabially by female wearers. In response thereto, several manufacturers have produced labial pads that are quite small in size in comparison to the prior devices described above. However, the construction of many of these devices appears to fail to recognize the wide range of variation that exists among women with regard to the location of their vaginal and urethral orifices within their vestibules. For example, some current devices often locate a widest portion of the absorbent core in the center of the device with a more narrow portion of the absorbent core located in the ends. Such devices afford less protection for the broad spectrum of women whose vaginal and urethral orifices are not located in the center of their vestibules. Other devices appear to provide a uniform distribution of absorbent core substantially throughout the longitudinal length of the device. However, the designs of many of these other devices typically fail to significantly enhance individualized fit and/or absorbent capacity.

SUMMARY

The present inventors have recognized the deficiencies and problems inherent in the prior art and in response thereto conducted intensive research in developing the innovative labial pads of the present invention. The inventors discovered that by situating more absorbent in at least one of the end regions rather than in the central region, their labial pads could be utilized by the broad spectrum of women whose vaginal and urethral openings are positioned in varying locations within their vestibules. The inventors also discovered that a narrowing in the width of the absorbent, at least in the central region of their labial pad, resulted in enhancing individualized fit and absorbent capacity.

In one embodiment of the present invention, an absorbent article is disclosed as having a fluid permeable cover, a liquid impermeable baffle and an absorbent. The absorbent is desirably situated between the cover and the baffle. The absorbent article has a principal longitudinal axis and a principal transverse axis, and is configured for disposition within the vestibule of a female wearer. The absorbent has a length, a widest portion, a width at the widest portion, a narrowest portion, a width at the narrowest portion, and a thickness. The absorbent also has first and second end regions and a central region disposed between the first and second end regions. In addition, the absorbent includes first and second spaced apart longitudinal sides, and first and second spaced apart transverse ends. The longitudinal sides together with the transverse ends generally form the periphery of the absorbent. Desirably, the widest portion of the absorbent is situated in a region other than the central region.

In another embodiment, an absorbent article is disclosed as including an absorbent and a liquid impermeable baffle. The absorbent article has a principal longitudinal axis and a principal transverse axis, and is configured for disposition within the vestibule of a female wearer. The absorbent has a length, a widest portion, a width at the widest portion, a narrowest portion, a width at the narrowest portion, and a thickness. The absorbent also has first and second end regions and a central region disposed between the first and second end regions. In addition, the absorbent includes first and second spaced apart longitudinal sides, and first and second spaced apart transverse ends. The longitudinal sides together with the transverse ends generally form the periphery of the absorbent. Desirably, the widest portion of the absorbent is situated in a region other than the central region.

In still another embodiment, an absorbent article is disclosed as having an absorbent configured for disposition within the vestibule of a female wearer. The absorbent has an upper surface, a principal longitudinal axis, a principal transverse axis, a length, a widest portion, a width at the widest portion, a narrowest portion, a width at the narrowest portion, and a thickness. The absorbent also has first and second end regions and a central region disposed between the first and second end regions. In addition, the absorbent includes first and second spaced apart longitudinal sides, and first and second spaced apart transverse ends. The longitudinal sides together with the transverse ends generally form the periphery of the absorbent. Desirably, the widest portion of the absorbent is situated in a region other than the central region.

DRAWINGS

The foregoing and other features, aspects and advantages of the present invention will become better understood with regard to the following description, appended claims and accompanying drawings where:

DESCRIPTION

Figure 1:
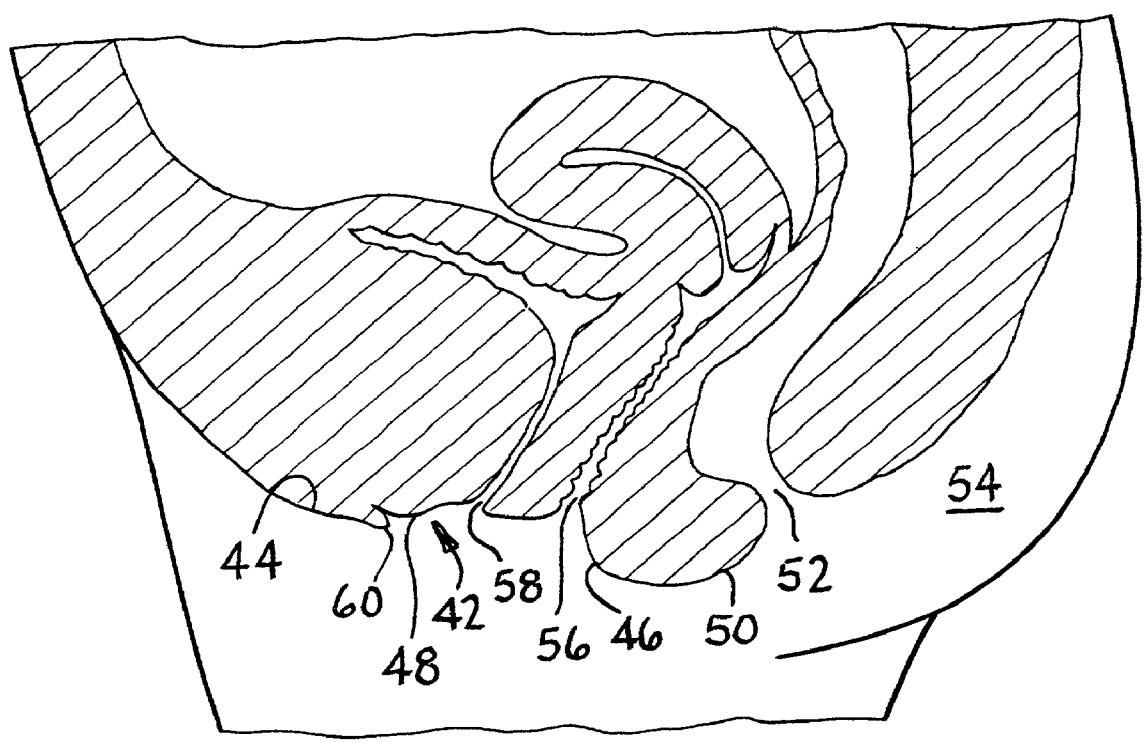
FIG. 1 is a simplified anatomical cross-sectional view of a human female illustrating the environment for an absorbent article such as a labial pad.
Figure 2:
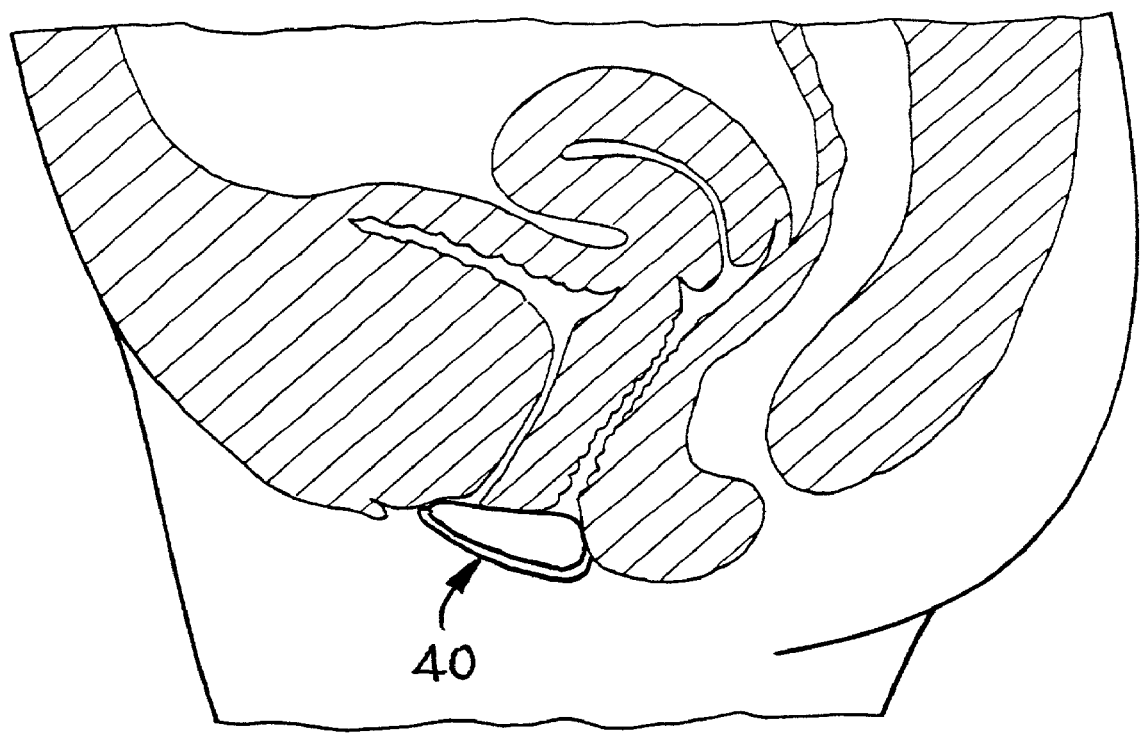
FIG. 2 is a simplified anatomical cross-sectional view of a human female illustrating a placement of an absorbent article, such as a labial pad, disposed in the vestibule of a wearer.

Turning to the figures of drawing, i.e., FIGS. 1 through 14, in each of which similar parts are identified with like reference characters, FIG. 2 illustrates diagrammatically an absorbent article, such as a labial pad, of the present invention, designated generally as 40, disposed within the vestibule of a wearer, designated generally as 42 (see also FIG. 1). As used herein, the term "labial pad" refers to a device having at least some absorbent components, and which is specifically configured for disposition in between the labia majora, extending at least partially into the vestibule (42) of a female wearer during use. For purposes of the ensuing description, the vestibule (42) is considered to be the region defined within the labia (not specifically shown in the figures herein) beginning at about a point lying caudally from the anterior labial commissure (44), extending rearward to the posterior labial commissure (46) and bounded inwardly by the floor (48) of the vestibule. One of skill in the art fully understands that there is a wide range of variation among women with respect to the relative size and shape of labia majora and labia minora as the same interrelatedly define the contour of the vestibule (42). For purposes of the present description, however, such differences will not specifically be addressed, it being recognized that in any event the disposition of the absorbent article (40) of the present invention into the vestibule (42) will necessitate placement between the labia majora regardless of any such consideration respecting the labia minora. Lying caudally of the vestibule (42) is the perineum (50) which leads to the anus (52) in the region of the buttocks (54). Within the vestibule (42) itself is located the principal urogenital members which, for purposes pertinent here, are constituted of the vaginal orifice (56), the urethral orifice (58), and the clitoris (60). Given the foregoing simplified review of this anatomical region, and to facilitate the present description, the vestibule (42) will be considered generally to be the region between the posterior labial commissure (46) and the clitoris (60), for convenience. For a more comprehensive description of this portion of the human female anatomy, however, attention is invited to *Anatomy of the Human Body* by Henry Gray, Thirtieth American Edition (Carmine D. Clemente ed., Lea & Febiger, 1985) at 1571-1581.

As can be seen with reference to the anatomical structure illustrated in FIGS. 1 and 2, the absorbent article (40) of the present invention is disposed at least partially within the vestibule (42) for at least partially occluding the same respecting fluid flow therefrom. In this regard, the predominant use of the absorbent article (40) is for the absorption of menstrual fluid emitted via the vaginal orifice (56); although the absorbent article of the present invention is equally well adapted to serve as a type of incontinence device for absorption of urine as occurs upon minor, female incontinence.

Figure 3:
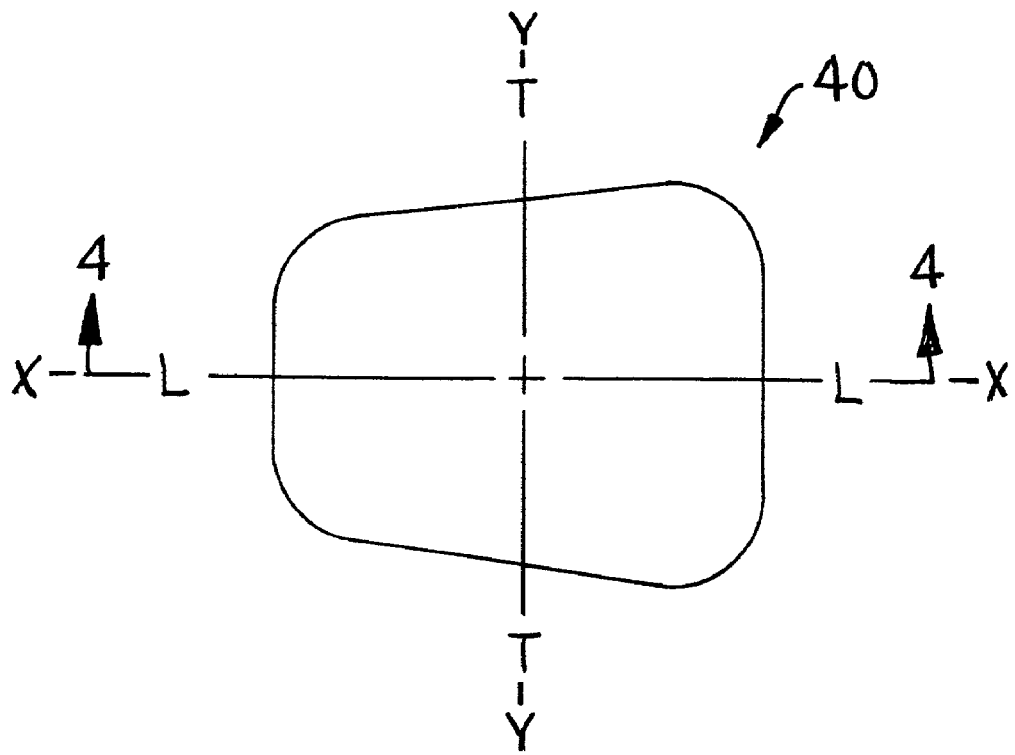
FIG. 3 is a top view illustrating an embodiment of an absorbent article of the present invention.
Figure 4:
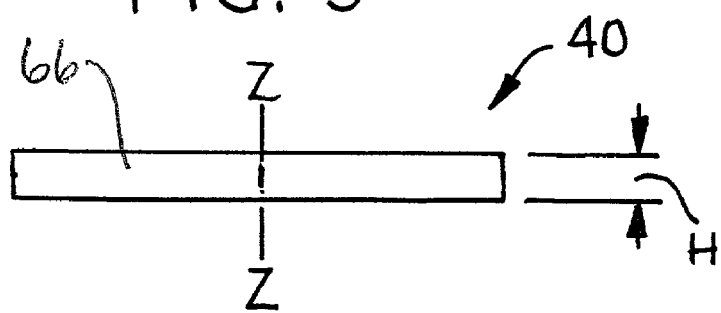
FIG. 4 is cross-sectional view of the embodiment illustrated in FIG. 3 taken along line 4-4 thereof.

The absorbent article (40) of the present invention, an embodiment of which is illustrated in FIG. 3, has a principal longitudinal axis (L) which generally runs along the x direction. As used herein, the term "longitudinal" refers to a line, axis or direction in the plane of the absorbent article (40) that is generally aligned with (e.g., approximately parallel to) a vertical plane that bisects a standing female wearer into left and right body halves when the absorbent article is in use. The longitudinal direction is generally illustrated in FIG. 3 by the x-axis. The absorbent article (40) also has a principal transverse axis (T). The terms "transverse," "lateral" or "y direction" as used herein generally refer to a line, axis or direction that is generally perpendicular to the longitudinal direction. The lateral direction is generally illustrated in FIG. 3 by the y-axis. The "z direction" is typically a line, axis or direction generally parallel to the vertical plane described above. The z direction is generally illustrated in FIG. 4 by the z-axis. The term "upper" refers generally to an orientation directed toward the wearer's head, while the terms "lower" or "downwardly" refer generally to an orientation directed toward the wearer's feet. For purposes of discussion herein, each layer of the absorbent article (40), e.g., a fluid permeable cover (62), a liquid impermeable baffle (64) and/or an absorbent (66), has an upper or body-facing surface and a lower surface also described as the surface opposed to the upper or body-facing surface.

Figure 5:
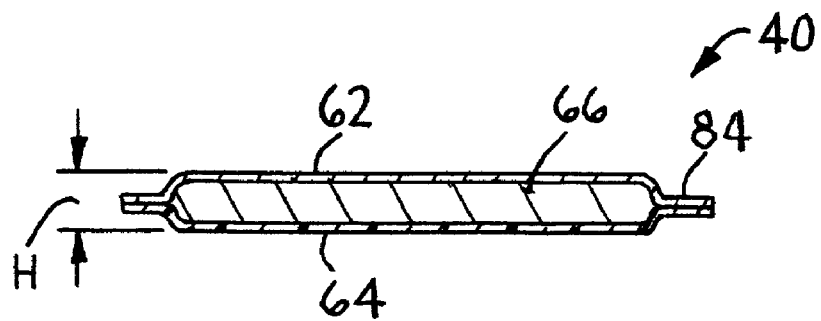
FIG. 5 is a cross-sectional view illustrating another embodiment of an absorbent article of the present invention.
Figure 6:
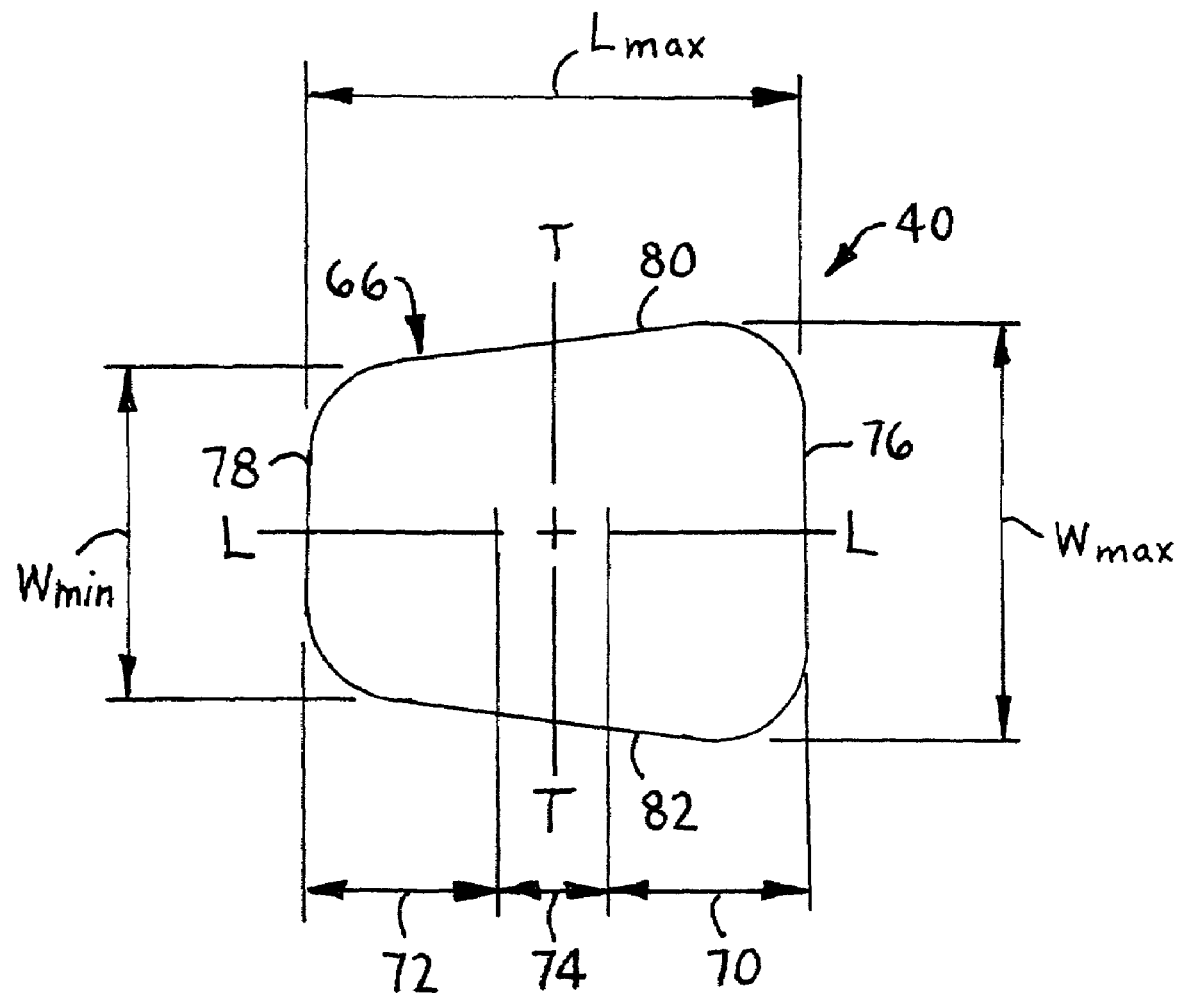
FIG. 6 is a top view illustrating an embodiment similar to that illustrated in FIG. 4.
Figure 7:
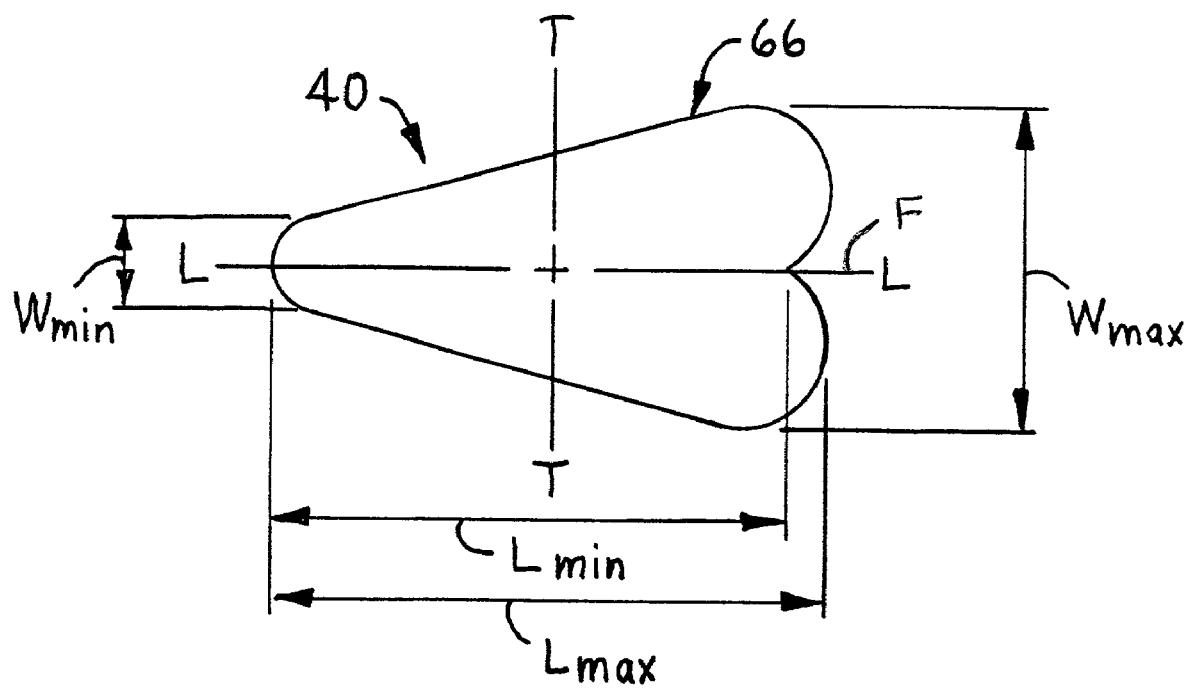
FIG. 7 is a top view illustrating yet another embodiment of an absorbent article of the present invention.
Figure 8:
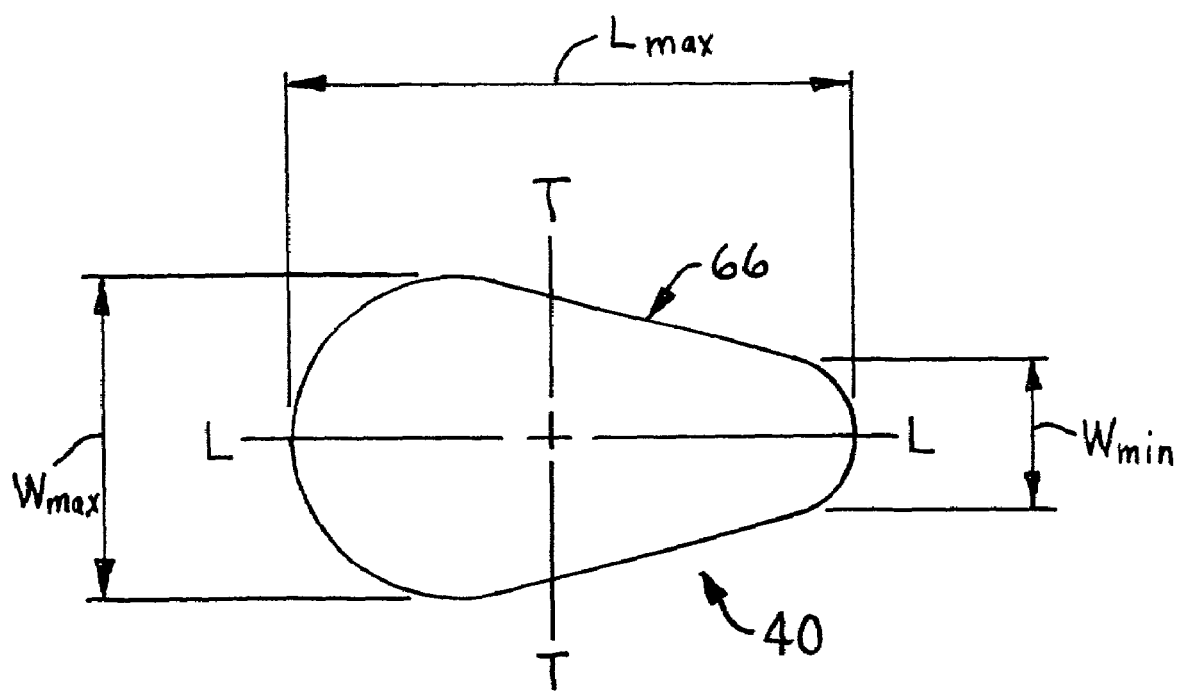
FIG. 8 is a top view illustrating still another embodiment of an absorbent article of the present invention.
Figure 9:
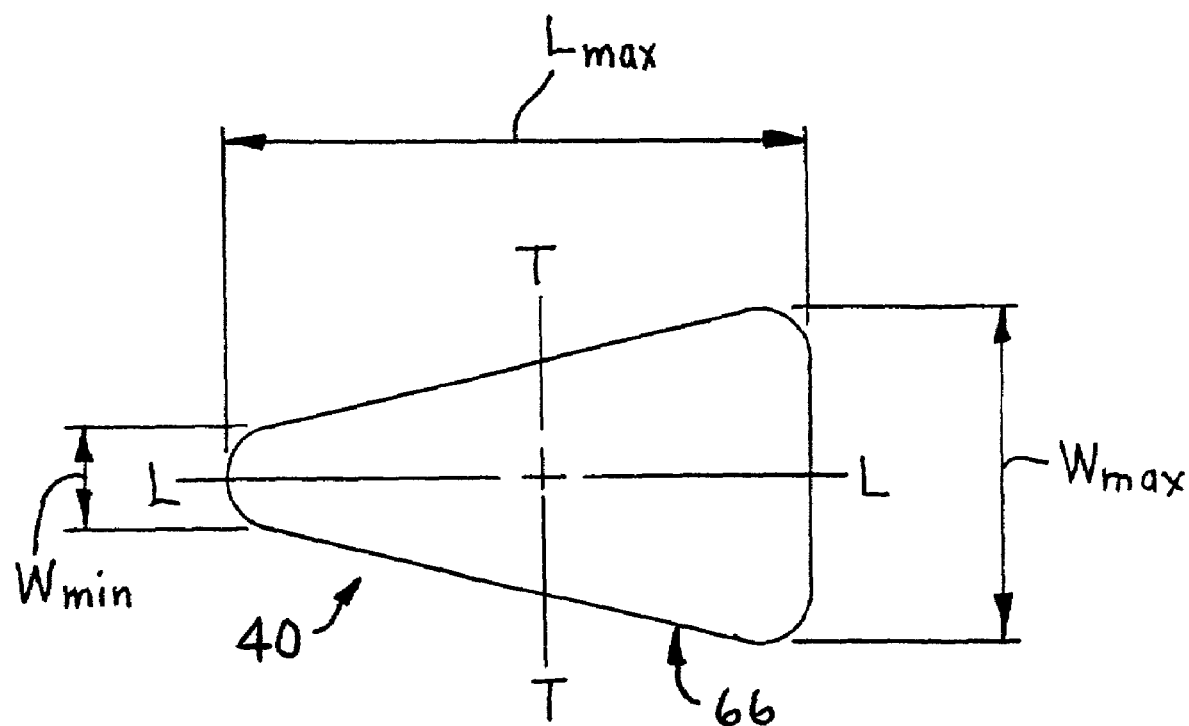
FIG. 9 is a top view illustrating an alternate embodiment of an absorbent article of the present invention.
Figure 10:
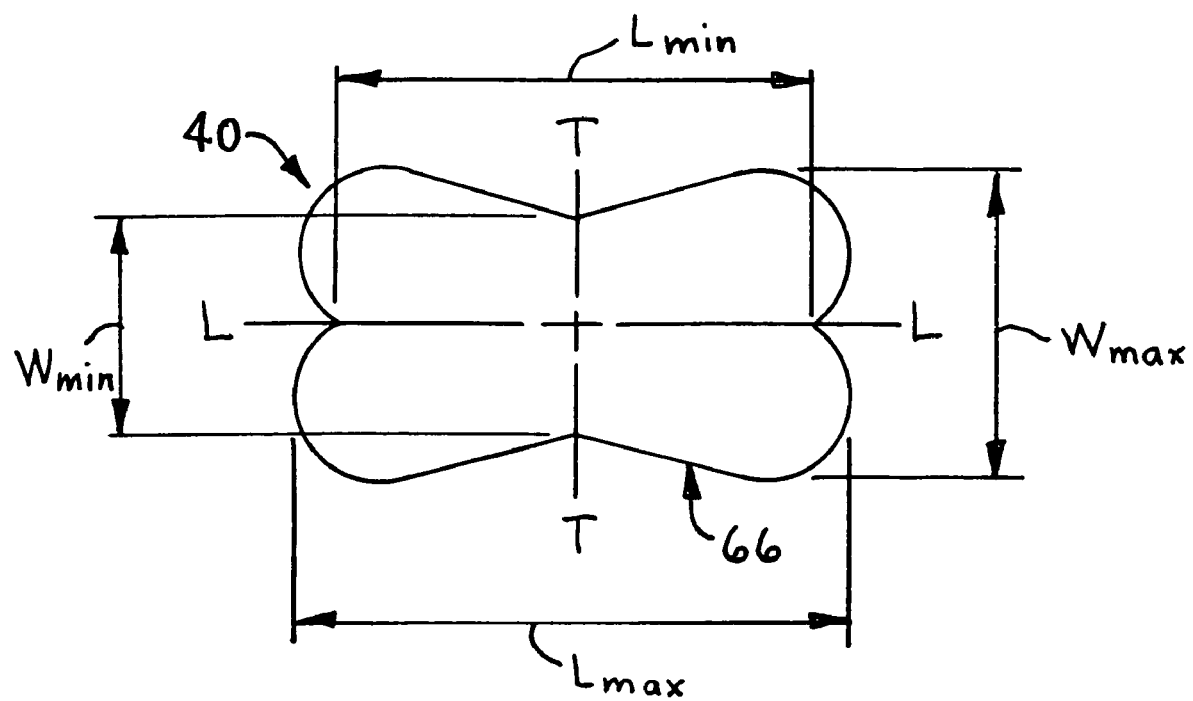
FIG. 10 is a top view illustrating another alternate embodiment of an absorbent article of the present invention.
Figure 11:
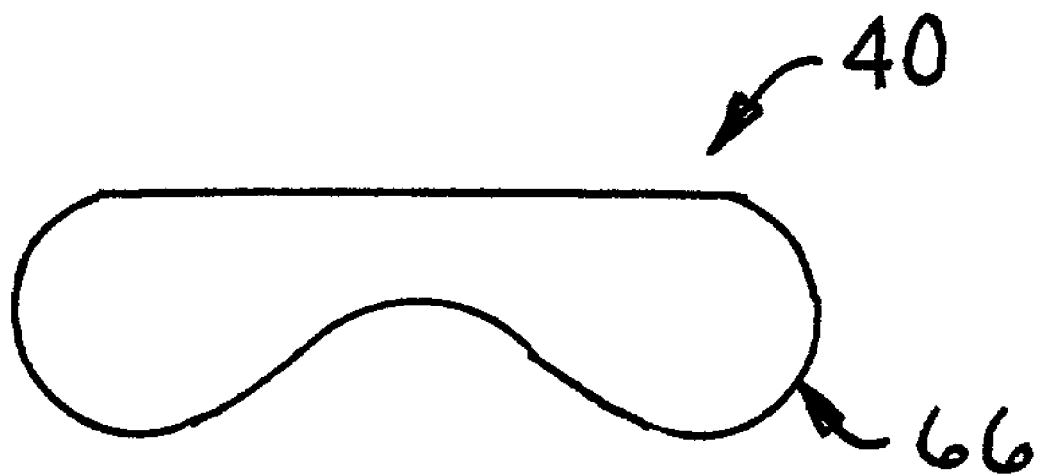
FIG. 11 is a cross-sectional view illustrating yet another alternate embodiment of an absorbent article of the present invention.

Turning now to FIG. 5, an absorbent article (40) is illustrated as including a fluid permeable cover (62), a liquid impermeable baffle (64) and an absorbent (66) situated between the cover and the baffle. As illustrated in FIG. 6, the absorbent (66) has a first end region (70), a second end region (72), and a central region (74) disposed between each end region. The absorbent article (40) should be of a suitable size and shape that allows at least a portion of the absorbent article to be disposed within the vestibule (42) of a female wearer. In addition, the absorbent article (40) desirably at least partially occludes and intercepts the flow of menstrual fluid, urine or other bodily exudates from the wearer's vaginal orifice (56) and/or urethral orifice (58).

The absorbent (66), and thus the absorbent article (40), generally displays a geometry extending between spaced apart first (76) and second (78) transverse end areas. The overall geometry is completed by noting that the absorbent (66), and thus the absorbent article (40), also includes spaced apart first (80) and second (82) longitudinal sides ranging between the transverse end areas (76, 78), these collectively sometimes being referred to herein as the perimetral sides (i.e., those defining the periphery).

The geometry of the absorbent (66) is a significant factor affecting the overall size and effectiveness of the absorbent article (40). In general, the absorbent (66) has a maximum width ($W_{max}$), measured along a line laying generally parallel to the principal transverse axis (T) and running from one longitudinal side to the opposing longitudinal side (80, 82), and a minimum width ($W_{min}$), measured along a line also laying generally parallel to the principal transverse axis (T) and running from one longitudinal side to the opposing longitudinal side (80, 82). The maximum width ($W_{max}$) of the absorbent (66) can be situated in the first (70) and/or second (72) end region(s), while the minimum width ($W_{min}$) of the absorbent (66) is situated in a region or regions other than the region or regions in which the maximum width ($W_{max}$) of the absorbent is situated. For example, when the maximum width ($W_{max}$) of the absorbent (66) is situated in the first end region (70), the minimum width ($W_{min}$) of the absorbent (66) can be situated in either the second end region (72), the central region (74), or in both the second end and central regions. Alternatively, when the maximum width ($W_{max}$) of the absorbent (66) is situated in the second end region (72), the minimum width ($W_{min}$) of the absorbent (66) can be situated in either the first end region (70), the central region (74), or in both the first end and central regions. In another alternative, when the maximum width ($W_{max}$) of the absorbent (66) is situated in both the first (70) and second (72) end regions, the minimum width ($W_{min}$) of the absorbent (66) is situated in the central region (74). With regard to the various embodiments of the absorbent article (40) of the present invention, it has been found (for reasons discussed further herein) that it is generally not desirable to have the maximum width of the absorbent (66) situated in the central region (74). The minimum width ($W_{min}$) of the absorbent (66) typically is no less than about 30; alternatively, no less than about 20; alternatively, no less than about 10; or alternatively, no less than about 5 mm. The maximum width ($W_{max}$) of the absorbent (66) typically is no greater than about 30; alternatively, no greater than about 40; alternatively, no greater than about 50; alternatively, no greater than about 60; or alternatively, no greater than about 70 mm. Thus, the absorbent (66) may have a width ranging between no less than about 5 mm up to no greater than about 70 mm; although the approximate width(s) of the absorbent may vary according to, inter alia, the general design and intended disposition of the absorbent article (40) within the vestibule (42) of a female wearer.

The absorbent (66) also has a maximum length ($L_{max}$), measured along a line laying generally parallel to the principal longitudinal axis (L) and running from one transverse end area to the other transverse end area (76, 78). The maximum length ($L_{max}$) of the absorbent (66) typically is no greater than about 40; alternatively, no greater than about 50; alternatively, no greater than about 60; alternatively, no greater than about 70; alternatively, no greater than about 80; alternatively, no greater than about 90; or alternatively, no greater than about 100 mm. The absorbent (66) may also have a minimum length ($L_{min}$), measured along a line also laying generally parallel to the principal longitudinal axis (L) and running from one transverse end area to the other transverse end area (76, 78). The minimum length ($L_{min}$) of the absorbent (66) typically is no less than about 100; alternatively, no less than about 90; alternatively, no less than about 80; alternatively, no less than about 70; alternatively, no less than about 60; alternatively, no less than about 50; or alternatively, no less than about 40 mm. Thus, the absorbent (66) may have a length ranging between no less than about 40 mm up to no greater than about 100 mm; although the approximate length(s) of the absorbent may vary according to, inter alia, the general design and intended disposition of the absorbent article (40) within the vestibule (42) of a female wearer. One of skill in the art will readily appreciate that certain embodiments of the absorbent (66), and thus certain embodiments of the absorbent article (40), of the present invention may have a minimum length ($L_{min}$) equal to its maximum length ($L_{max}$). In such instances, as illustrated at least in FIGS. 6, 8 and 9, reference is generally made only to the maximum length ($L_{max}$). Embodiments of an absorbent (66), and thus embodiments of an absorbent article (40), having a maximum length ($L_{max}$) not equal to its minimum length ($L_{min}$) are illustrated at least in FIGS. 7 and 10.

The first end region (70) and the second end region (72) each minimally extend outwardly from the central region (74) toward the transverse end areas (76 and 78, respectively) of the absorbent (66) a distance of no less than about 30; alternatively, no less than about 20; or alternatively, no less than about 10% of the maximum length ($L_{max}$) of the absorbent. The first end region (70) and the second end region (72) each maximally extend outwardly from the central region (74) toward the transverse end areas (76 and 78, respectively) of the absorbent (66) a distance of no greater than about 20; alternatively, no greater than about 30; or alternatively, no greater than about 40% of the maximum length ($L_{max}$) of the absorbent. Thus, the end regions (70, 72) may occupy from a minimum of about 20% up to a maximum of about 80% of the maximum length ($L_{max}$) of the absorbent (66); although the approximate size of the first and second end regions may vary according to, inter alia, the general design and intended disposition of the absorbent article (40) within the vestibule (42) of a female wearer.

The absorbent article (40) of the present invention is desirably provided with sufficient capacity to absorb and retain the intended amount and type of bodily exudate(s). The absorbent capacity is provided by a fluid retentive core or absorbent generally identified as 66. For at least menstrual fluid, the absorbent (66) desirably has a minimum capacity of no less than about 19; alternatively, no less than about 18; alternatively, no less than about 17; alternatively, no less than about 16; alternatively, no less than about 15; alternatively, no less than about 14; alternatively, no less than about 13; alternatively, no less than about 12; alternatively, no less than about 11; alternatively, no less than about 10; alternatively, no less than about 9; alternatively, no less than about 8; alternatively, no less than about 7; alternatively, no less than about 6; alternatively, no less than about 5; alternatively, no less than about 4; alternatively, no less than about 3; alternatively, no less than about 2; or alternatively, no less than about 1 g/g. The absorbent (66) also may have a maximum capacity of no greater than about 5; alternatively, no greater than about 6; alternatively, no greater than about 7; alternatively, no greater than about 8; alternatively, no greater than about 9; alternatively, no greater than about 10; alternatively, no greater than about 11; alternatively, no greater than about 12; alternatively, no greater than about 13; alternatively, no greater than about 14; alternatively, no greater than about 15; alternatively, no greater than about 16; alternatively, no greater than about 17; alternatively, no greater than about 18; alternatively, no greater than about 19; alternatively, no greater than about 20; alternatively, no greater than about 25; or alternatively, no greater than about 30 g/g. Thus, the absorbent (66) may have an absorbent capacity ranging between no less than about 1 g/g up to no greater than about 30 g/g; although the approximate capacity of the absorbent may vary according to, inter alia, the general design and intended disposition of the absorbent article (40) within the vestibule (42) of a female wearer. One of skill in the art will readily realize that the addition of superabsorbent polymer(s) or coated superabsorbent polymer(s) to the absorbent (66) typically has the effect of substantially increasing the absorbent capacity.

Describing the individual elements in greater detail, the absorbent (66) has an upper or body-facing surface and a lower surface (or surface opposed to the upper or body-facing surface) and may include any material capable of absorbing and/or adsorbing and thereafter retaining the intended bodily exudate(s). Suitable materials are also generally hydrophilic, compressible and conformable. The absorbent (66) may be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester and polypropylene fibers, absorbent foams, absorbent sponges, superabsorbent polymers, coated superabsorbent polymers, fibrous bundles or nits, or any equivalent material or combination of materials. Also suitable for use would be hydrophobic material that has been rendered hydrophilic according to any of a number of known methods for so doing. The total absorbent capacity of the absorbent (66) should, however, be compatible with the design exudate loading and the intended use of the absorbent article (40). Further, the size and absorbent capacity of the absorbent (66) may be varied. Therefore, the dimension, shape, and configuration of the absorbent (66) may be varied (e.g., the absorbent may have a varying thickness as illustrated at least in FIGS. 11 and 12, or a hydrophilic gradient, or may contain superabsorbent polymer(s) and the like).

The absorbent (66) generally has a thickness, caliper or height (H), as illustrated at least in FIG. 4, measured along a line lying generally parallel to the z-axis. The minimum thickness of the absorbent (66) typically is no less than about 9; alternatively, no less than about 8; alternatively, no less than about 7; alternatively, no less than about 6; alternatively, no less than about 5; alternatively, no less than about 4; alternatively , no less than about 3; alternatively, no less than about 2; alternatively, no less than about 1; or alternatively, no less than about 0.5 mm. The maximum thickness of the absorbent (66) typically is no greater than about 2; alternatively, no greater than about 3; alternatively, no greater than about 4; alternatively, no greater than about 5; alternatively, no greater than about 6; alternatively, no greater than about 7; alternatively, no greater than about 8; alternatively, no greater than about 9; or alternatively, no greater than about 10 mm. Thus, the absorbent (66) may have a thickness of about 10 mm or less; although the approximate thickness of the absorbent may vary according to, inter alia, the general design and intended disposition of the absorbent article (40) within the vestibule (42) of a female wearer.

The absorbent (66) desirably also has a relatively low density which is deemed desirable for comfort. Generally, the absorbent has a density of less than about 0.5 g/cc. Stated differently, the absorbent (66) typically has a maximum density of no greater than about 0.5; alternatively, no greater than about 0.4; alternatively, no greater than about 0.3; alternatively, no greater than about 0.2; alternatively, no greater than about 0.1; alternatively, no greater than about 0.09; alternatively, no greater than about 0.08; alternatively, no greater than about 0.07; alternatively, no greater than about 0.06; alternatively, no greater than about 0.05; alternatively, no greater than about 0.04; alternatively, no greater than about 0.03; or alternatively, no greater than about 0.02 g/cc. The absorbent (66) generally also has a minimum density of typically no less than about 0.01; alternatively no less than about 0.02; alternatively, no less than about 0.03; alternatively, no less than about 0.04; alternatively, no less than about 0.05; alternatively, no less than about 0.06; alternatively, no less than about 0.07; alternatively, no less than about 0.08; alternatively, no less than about 0.09; alternatively, no less than about 0.1; alternatively, no less than about 0.2; alternatively, no less than about 0.3; or alternatively, no less than about 0.4 g/cc. Thus, the density of the absorbent (66) may range up to about 0.5 g/cc; although the approximate density of the absorbent may vary according to, inter alia, the general design and intended disposition of the absorbent article (40) within the vestibule (42) of a female wearer.

The absorbent (66) also desirably has a basis weight of less than about 600 grams per square meter (gsm). Stated differently, the absorbent (66) typically has a maximum basis weight of no greater than about 600; alternatively, no greater than about 500; alternatively, no greater than about 400; alternatively, no greater than about 300; alternatively, no greater than about 200; or alternatively, no greater than about 100 gsm. Generally, the absorbent (66) also has a minimum basis weight of typically no less than about 0.1; alternatively, no less than about 50; alternatively, no less than about 100; alternatively, no less than about 150; alternatively, no less than about 200; alternatively, no less than about 250; alternatively, no less than about 300; alternatively, no less than about 350; alternatively, no less than about 400; alternatively, no less than about 450; alternatively, no less than about 500; or alternatively, no less than about 550 gsm. Thus, the absorbent (66) may have a basis weight of about 600 gsm or less; although the approximate basis weight of the absorbent may vary according to, inter alia, the general design and intended disposition of the absorbent article (40) within the vestibule (42) of a female wearer. A specific example of a suitable absorbent would be similar to a coform material made of a blend of polypropylene and cellulose fibers and used in KOTEX® maxi pantiliners and obtainable from Kimberly-Clark Corporation, Neenah, Wis., USA.

The optional baffle (64) typically resides on the lower surface of the absorbent (66) and may be constructed from any desired material that is liquid-impermeable. Desirably, the baffle (64) will permit the passage of air and moisture vapor out of the absorbent (66), while blocking the passage of bodily fluid(s). An example of a suitable baffle material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render them liquid-impermeable. An example of another suitable material is a closed cell polyolefin foam. A closed cell polyethylene foam may also work well.

The baffle (64) may be maintained in secured relation with the absorbent (66) by bonding all or a portion of the adjacent surfaces to one another. A variety of bonding methods known to one of skill in the art may be utilized to achieve any such secured relation. Examples of such methods include, but are not limited to, ultrasonics, thermal bonding, or the application of adhesives in a variety of patterns between the two adjoining surfaces. A specific example of a baffle material would be similar to a polyethylene film used on KOTEX® pantiliners and obtainable from Pliant Corporation, Schaumburg, Ill., USA.

The optional fluid permeable cover (62) has an upper surface and a lower surface, with the upper surface typically contacting the body of the wearer and receiving bodily exudate(s). The cover (62) desirably is made of a material that is flexible and non-irritating to the tissues within the vestibule (42) of a female wearer. As used herein, the term "flexible" is intended to refer to materials which are compliant and readily conform to the bodily surface(s) or respond by easily deforming in the presence of external forces.

The cover (62) is provided for comfort and conformability and functions to direct bodily exudate(s) away from the body and toward the absorbent (66). The cover (62) should retain little or no liquid in its structure so that it provides a relatively comfortable and non-irritating surface next to the tissues within the vestibule (42) of a female wearer. The cover (62) can be constructed of any woven or nonwoven material which is also easily penetrated by bodily fluids contacting its surface. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs and net material also work well. A specific example of a suitable cover material would be similar to a bonded carded web made of polypropylene and polyethylene used as a cover stock for KOTEX® pantiliners and obtainable from Sandler Corporation, Germany. Other examples of suitable materials are composite materials of a polymer and a nonwoven fabric material. The composite materials are typically in the form of integral sheets generally formed by the extrusion of a polymer onto a web of spunbond material. The fluid permeable cover (62) can also contain a plurality of apertures (not shown) formed therein which are intended to increase the rate at which bodily fluid(s) can penetrate into the absorbent (66).

A physiologically hydrous cover material is also suitable for use in the present invention. As used herein, the term "physiologically hydrous" is intended to connote a cover material which maintains a suitably moist interface between the tissues of the vestibule (42) and the absorbent article (40) when disposed in that vestibular environment; one that is benign respecting the requirements of comfort associated with the interposition of fabric or fabric-like structures within the moist tissue environment of the vestibule, keeping in mind as well the self-evident factor that the absorbent article is receiving bodily fluid(s) migrating through the vestibule and must conduct the same to the absorbent (66). Thus, while not "hydrous" in the classic sense prior to use (inasmuch as the cover will be dry at that time) the cover (62) maintains (or at least does not interfere with the maintenance of) the proper moisture level or balance required within the vestibule (42).

The cover (62) can also have at least a portion of the surface treated with a surfactant to render the cover more hydrophilic. This results in permitting the insulting bodily fluid(s) to more readily penetrate the cover (62). The surfactant may also diminish the likelihood that the insulting bodily fluid(s), such as menstrual fluid, will flow off the cover (62) rather than being absorbed by the absorbent (66). One suitable approach provides for the surfactant to be substantially evenly distributed across at least a portion of the upper surface of the cover (62) that overlays the upper surface of the absorbent (66).

The cover (62) may be maintained in secured relation with the absorbent (66) by bonding all or a portion of the adjacent surfaces to one another. A variety of bonding methods known to one of skill in the art may be utilized to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover (62) typically resides on the upper surface of the absorbent (66), but alternatively can surround and partially or entirely enclose the absorbent. Alternatively, the cover (62) and the baffle (64) can have peripheries which extend outward beyond the periphery of the absorbent (66) and can be peripherally joined together to form an edge (84), as illustrated at least in FIG. 5. Utilizing known techniques, such as, for example, gluing, crimping, hot-sealing or the like, the edge (84) may be formed either entirely, so that the entire periphery of the absorbent (66) is circumscribed by their joinder, or the cover (62) and the baffle (64) can be partially peripherally joined. To minimize the possibility of irritation and/or discomfort to the wearer of the absorbent article (40), it is desired that the edge (84) and at least the area of the absorbent article immediately adjacent the edge be soft, compressible and conformable. Desirably, any edge (84) so formed shall have a width no greater than about 10; alternatively, no greater than about 9; alternatively, no greater than about 8; alternatively, no greater than about 7; alternatively, no greater than about 6; alternatively, no greater than about 5; alternatively, no greater than about 4; alternatively, no greater than about 3; alternatively, no greater than about 2; or alternatively, no greater than about 1 mm. In addition, any edge (84) so formed shall desirably have a width of no less than about 0.5; alternatively, no less than about 1; alternatively, no less than about 2; alternatively, no less than about 3; alternatively, no less than about 4; alternatively, no less than about 5; alternatively, no less than about 6; alternatively, no less than about 7; alternatively, no less than about 8; or alternatively, no less than about 9 mm. Thus, any edge (84) so formed may have a width ranging from no less than about 0.5 mm up to no greater than about 10 mm; although the approximate width of any edge may vary according to, inter alia, the general design and intended disposition of the absorbent article (40) within the vestibule (42) of a female wearer. In other embodiments, the cover (62) and/or the baffle (64) can have a periphery that is coterminous with the periphery of the absorbent (66).

Positioned either on or substantially parallel to the principal longitudinal axis (L) of the absorbent (66), is, optionally, a desired axis of flexure (F). A desired axis of flexure (F) generally runs in the longitudinal direction, i.e., along the x direction, and may be off center from the principal longitudinal axis (L) a distance of no greater than about 10; alternatively, no greater than about 9; alternatively, no greater than about 8; alternatively, no greater than about 7; alternatively, no greater than about 6; alternatively, no greater than about 5; alternatively, no greater than about 4; alternatively, no greater than about 3; alternatively, no greater than about 2; or alternatively, no greater than about 1 mm. Desirably, a desired axis of flexure (F) is aligned along the principal longitudinal axis (L). A desired axis of flexure (F) typically minimally extends longitudinally no less than about 90; alternatively, no less than about 80; alternatively, no less than about 70; alternatively, no less than about 60; alternatively, no less than about 50; or alternatively, no less than about 40% of the maximum length ($L_{max}$) of the absorbent (66). A desired axis of flexure (F) typically extends longitudinally no greater than about 50; alternatively, no greater than about 60; alternatively, no greater than about 70; alternatively, no greater than about 80; alternatively, no greater than about 90; or alternatively, no greater than about 100% of the maximum length ($L_{max}$) of the absorbent (66). A desired axis of flexure (F) may result naturally from the dimensions, shape, and/or configuration of the absorbent (66), or the absorbent may be imparted with a weakened axis or region to create a desired axis of flexure. A desired axis of flexure (F) may also be formed by any of the techniques known to one of skill in the art, including, for example, scoring, pre-folding, slitting, embossing, or the like. Although a desired axis of flexure (F) is described herein as residing in the absorbent (66), one of skill in the art will readily appreciate that a desired axis of flexure may be formed in either the cover (62), the baffle (64) and/or the absorbent; the cover and the baffle; the cover and the absorbent; or the baffle and the absorbent. When present, a desired axis of flexure (F) typically allows an absorbent article (40) to be folded more easily prior to disposition within the vestibule (42) of a female wearer.

The desired geometries of the absorbent article (40) (i.e., those geometries which generally do not have the maximum width ($W_{max}$) of the absorbent (66) situated in the central region (74)) recognize that a significant number of women do not have vaginal and urethral orifices located at the midpoint of a line extending longitudinally between the posterior labial commissure (46) and the clitoris (60). Although many drawings of the female anatomy illustrate the urethral orifice (58) near the anterior labial commissure (44) and the vaginal orifice (56) near the posterior labial commissure (46), with the vaginal orifice (56) being significantly larger than the urethral orifice (58), there is significant variation in the size and location of both orifices. The longitudinal distance between the urethral orifice (58) and the vaginal orifice (56) can vary significantly, as can the longitudinal distance between the clitoris (60) and the urethral orifice (58) and the longitudinal distance between the vaginal orifice (56) and the posterior labial commissure (46). For example, the longitudinal distance between the clitoris (60) and the urethral orifice (58) may range from about 0.5 to about 4 cm, while the longitudinal distance between the vaginal orifice (56) and the posterior labial commissure (46) may range from about 1 to about 5 cm. In addition to the variation in the previously described longitudinal distances, the longitudinal distance between the urethral (58) and vaginal (56) orifices can range from about 0.5 to about 4.5 cm. Moreover, the length of the labia may both vary significantly. Mindful of such variations, the absorbent article (40) of the present invention allows the wearer to position an end region having the maximum width of the absorbent (66) adjacent the desired orifice to intercept the intended bodily exudate(s). For example, if the intended bodily exudate is menstrual fluid and the vaginal orifice (56) is located closer to the posterior labial commissure (46), the wearer of an absorbent article similar to that illustrated in FIG. 6 may position the first end region (70) (having the maximum width ($W_{max}$) of the absorbent (66)) under the vaginal orifice and thus closer to the posterior labial commissure. Alternatively, for example, if the intended bodily exudate is menstrual fluid and the vaginal orifice (56) is located closer to the clitoris (60), the wearer of an absorbent article similar to that illustrated in FIG. 6 may position the first end region (70) (having the maximum width ($W_{max}$) of the absorbent (66)) under the vaginal orifice and thus closer to the clitoris. Alternatively still, for example, if the intended bodily exudate is menstrual fluid and the vaginal orifice (56) is located at the midpoint of a line extending longitudinally between the clitoris (60) and the posterior labial commissure (46), the wearer may select and position an absorbent article (40) having an appropriate geometry with the maximum width ($W_{max}$) of the absorbent (66) under the vaginal orifice with the region(s) having the minimum width ($W_{min}$) of the absorbent oriented closer to either the clitoris or the posterior labial commissure, whichever is most comfortable for the female wearer. Consequently, the various embodiments of the absorbent article (40) of the present invention may be reversibly disposed in the vestibule (42) of a female wearer. Such reversibility allows for a female wearer to maximize comfort and conformability by disposing the absorbent article (40) within her vestibule in an orientation which results in a customized fit best suited to the location of her principal urogenital members. The capability of affording a customized fit also allows individualized positioning or placement of the absorbent article (40) within the female wearer's vestibule (42). By allowing such individualized placement, the female wearer is able to dispose the absorbent article within her vestibule in an orientation where, in her opinion, (i) the most comfortable fit is obtained and (ii) she needs the maximum width ($W_{max}$) of the absorbent (66). Without desiring to be bound by theory, it is believed that the likelihood of leakage is also minimized by affording a female wearer the opportunity to dispose the absorbent article (40) within her vestibule in an orientation that places the maximum width ($W_{max}$) of the absorbent (66) in close proximity to the chosen orifice to absorb and/or adsorb the intended exudate(s).

An absorbent article (40) with the desired geometry of the present invention, when folded along the principal longitudinal axis (L), will have a profile in which the highest point along the principal longitudinal axis (L) (as measured in the z direction) is situated in at least the first end region (70) and/or the second end region (72) (i.e., is not situated in the central region (74)). Even when not folded, however, the absorbent article (40) has a thickness, caliper or height (H), as illustrated at least in FIGS. 4 and 5, measured along a line laying generally parallel to the z-axis. The minimum thickness of the absorbent article (40) typically is no less than about 9; alternatively, no less than about 8; alternatively, no less than about 7; alternatively, no less than about 6; alternatively, no less than about 5; alternatively, no less than about 4; alternatively, no less than about 3; alternatively, no less than about 2; alternatively, no less than about 1; or alternatively, no less than about 0.5 mm. The maximum thickness of the absorbent article (40) typically is no greater than about 1; alternatively, no greater than about 2; alternatively, no greater than about 3; alternatively, no greater than about 4; alternatively, no greater than about 5; alternatively, no greater than about 6; alternatively, no greater than about 7; alternatively, no greater than about 8; alternatively, no greater than about 9; or alternatively, no greater than about 10 mm. Thus, the absorbent article (40) may have a thickness of about 10 mm or less; although the approximate thickness of the absorbent article may vary according to, inter alia, the general design and intended disposition of the absorbent article within the vestibule (42) of a female wearer.

Figure 12:
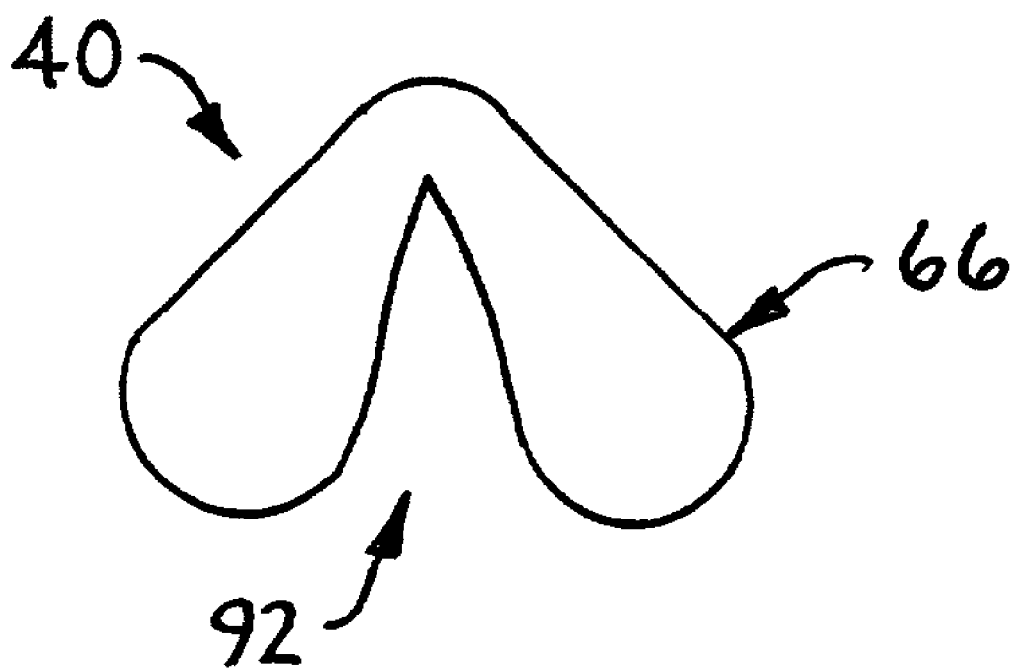
FIG. 12 is a cross-sectional view illustrating the embodiment of FIG. 11 in a folded position.
Figure 13:
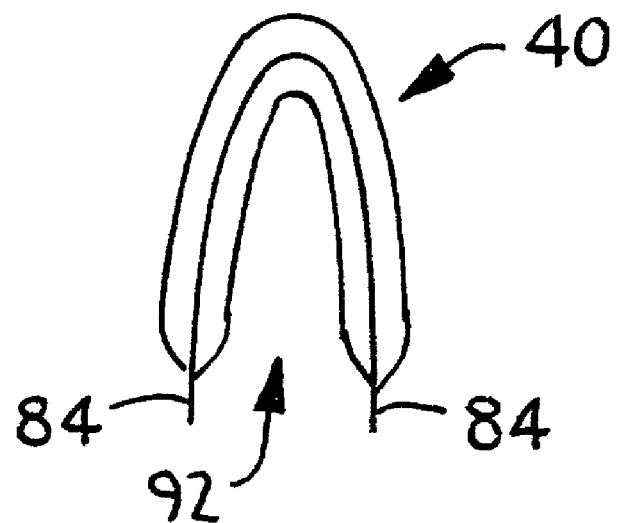
FIG. 13 illustrates an enlarged view of a further embodiment of an absorbent article of the present invention folded substantially about a principal axis.
Figure 14:
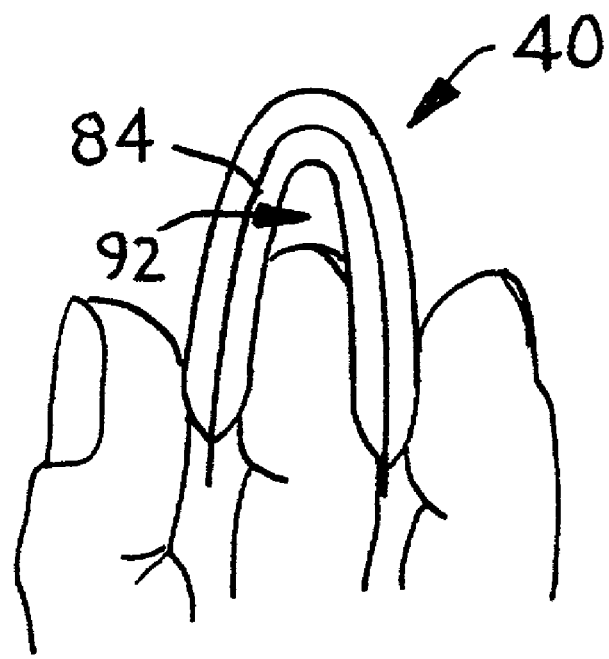
FIG. 14 illustrates an exaggerated enlarged view of yet another further embodiment of an absorbent article of the present invention folded substantially about a principal axis and being grasped for disposition in the vestibule by the wearer's fingers.

The absorbent article (40) typically is folded along an axis lying on or positioned parallel to the principal longitudinal axis (L), as illustrated at least in FIGS. 12, 13 and 14, prior to disposition within the vestibule (42) of the female wearer. When folded along such an axis, the absorbent article (40) will form a recess (92) which protects the wearer's finger(s) from soiling when the absorbent article is disposed within the vestibule (42). Once inserted, the absorbent article (40) may have a tendency to unfold in an attempt to fill the vestibule and thus maintain the upper surface of the absorbent article in contact with the tissues of the vestibule (42). The absorbent article (40) may be resiliently biased along the axis about which it is folded to increase the tendency of the absorbent article to unfold. Alternatively, the absorbent (66) of the absorbent article (40) may be thicker along its longitudinal edges, as illustrated at least in FIGS. 11 and 12, thus also demonstrating a biasing effect, if desired, which is typically intended to allow the upper surface of the absorbent article (40) to contact the tissues of the vestibule (42). An absorbent article (40) designed as described herein, however, does not necessarily require any additional features to maintain contact with the tissues of the vestibule (42) of the female wearer. The naturally moist surfaces of the tissues of the vestibule (42) typically demonstrate a tendency to maintain contact with the upper surface of the absorbent article (40).

As noted above, the wearer may fold the absorbent article (40) along an axis lying on or positioned parallel to the principal longitudinal axis (L) prior to disposition within the vestibule (42). The wearer may, therefore, hold the folded absorbent article (40) at the longitudinal sides as illustrated at least in FIG. 14. The absorbent article (40) may then be disposed within the vestibule (42) by the wearer exerting a force with a finger or fingers positioned in the recess (92) formed by the folded absorbent article.

Although various versions or embodiments of the present invention have been disclosed and described in considerable detail, other embodiments are possible. Consequently, the spirit and scope of the appended claims should not be limited to the illustration and description of the various embodiments contained herein.

What is claimed is:

1. An absorbent article (40) comprising a fluid permeable cover (62), a liquid impermeable baffle (64) and an absorbent (66) situated between the cover and the baffle, the absorbent article having a principal longitudinal axis and a principal transverse axis, and being configured to provide a labial pad for disposition within the vestibule of a female wearer, the absorbent having a maximum longitudinal length of no greater than about 100 mm extending from a first transverse end (76) to a spaced apart second transverse end (78), a body-facing surface of the absorbent having a minimum longitudinal length ($L_{min}$) that lies generally along said principal longitudinal axis from said first transverse end area to said second transverse end area and is less than said maximum longitudinal length, a maximum width of no greater than about 70 mm, a widest portion, a width at the widest portion, a narrowest portion, a width at the narrowest portion which is smaller than said width at the widest portion, a maximum thickness of no greater than about 10 mm, first (70) and second (72) end regions and a central region (74) disposed between the first and second end regions, and first (80) and second (82) spaced apart longitudinal sides, the longitudinal sides together with the transverse ends generally forming the periphery of the absorbent, wherein the widest portion of the absorbent is not situated in the central region, and the article is to be folded parallel to said longitudinal axis prior to disposition within the vestibule of the wearer.

2. The absorbent article of claim 1, wherein the widest portion of the absorbent is situated in the first end region.

3. The absorbent article of claim 2, wherein the narrowest portion of the absorbent is situated in said central region of the absorbent; a second widest portion of the absorbent has a width and is situated in the second end region of the absorbent, and said width at the narrowest portion is smaller than said width of said second widest portion of the absorbent.

4. The absorbent article of claim 1, wherein the widest portion of the absorbent is situated in the second end region.

5. The absorbent article of claim 1, wherein the cover and the baffle have peripheries which are coterminous with the periphery of the absorbent.

6. The absorbent article of claim 1, wherein the cover and the baffle have peripheries which extend outward beyond the periphery of the absorbent.

7. The absorbent article of claim 6, wherein the peripheries of the cover and the baffle are at least partially peripherally joined to form an edge (84).

8. The absorbent article of claim 1, wherein the absorbent further comprises a superabsorbent polymer.

9. An absorbent article (40) comprising an absorbent (66) and a liquid impermeable baffle (64), the absorbent article having a principal longitudinal axis and a principal transverse axis, and being configured to provide a labial pad for disposition within the vestibule of a female wearer, the absorbent having a maximum longitudinal length of no greater than about 100 mm extending from a first transverse end (76) to a spaced apart second transverse end (78), a body-facing surface of the absorbent having a minimum longitudinal length ($L_{min}$) that lies generally along said principal longitudinal axis from said first transverse end to said second transverse area and is less than said maximum longitudinal length, a maximum width of no greater than about 70 mm, a widest portion, a width at the widest portion, a narrowest portion, a width at the narrowest portion which is smaller than said width at the narrowest portion, a maximum thickness of no greater than about 10 mm, first (70) and second (72) end regions and a central region (74) disposed between the first and second end regions, and first (80) and second (82) spaced apart longitudinal sides, the longitudinal sides together with the transverse ends generally forming the periphery of the absorbent, wherein the widest portion of the absorbent is not situated in the central region, and the article is to be folded parallel to said longitudinal axis prior to disposition within the vestibule of the wearer.

10. The absorbent article of claim 9, wherein the widest portion of the absorbent is situated in the first end region.

11. The absorbent article of claim 10, wherein the narrowest portion of the absorbent is situated in said central region of the absorbent, a second widest portion of the absorbent is situated in the second end region of the absorbent, and said width of the narrowest portion is smaller than said width of the second widest portion.

12. The absorbent article of claim 9, wherein the widest portion of the absorbent is situated in the second end region.

13. The absorbent article of claim 9, wherein the baffle has a periphery which is coterminous with the periphery of the absorbent.

14. The absorbent article of claim 13, further comprising a fluid permeable cover (62), the cover having a periphery which is coterminous with the periphery of the absorbent.

15. The absorbent article of claim 9, further comprising a fluid permeable cover (62).

16. The absorbent article of claim 15, wherein the cover encloses the absorbent.

17. The absorbent article of claim 9, wherein the absorbent further comprises a superabsorbent polymer.

18. An absorbent article (40) having a longitudinal axis, said article comprising an absorbent (66) configured to provide a labial pad for disposition within the vestibule of a female wearer, a widest portion, a maximum width of no greater than about 70 mm, a maximum thickness of no greater than about 10 mm, first (70) and second (72) end regions and a central region (74) disposed between the first and second end regions, first (80) and second (82) spaced apart longitudinal sides, and first (76) and second (78) spaced apart transverse ends, the longitudinal sides together with the transverse ends generally forming the periphery of the absorbent, wherein
the absorbent has a maximum longitudinal length of no greater than about 100 mm extending from said first transverse end (76) to said second transverse end (78), a body-facing surface of the absorbent has a minimum longitudinal length ($L_{min}$) that extends generally along said principal longitudinal axis from said first transverse end to said second transverse area and is less than said maximum longitudinal length, the widest portion of the absorbent is situated in the first end region, a narrowest portion of the absorbent has a narrowest width situated in the central region of the absorbent, a second widest portion of the absorbent has a second widest width situated in the second end region of the absorbent, the width of the narrowest portion is smaller than the width of the second widest portion, and the article is configured to be folded parallel to said longitudinal axis prior to disposition within the vestibule of the wearer.

19. The absorbent article of claim 18, wherein the absorbent has an upper surface and a fluid permeable cover (62) residing on the upper surface of the absorbent.

20. The absorbent article of claim 18, further comprising a fluid permeable cover (62) surrounding the absorbent.

21. The absorbent article of claim 20, wherein the cover partially encloses the absorbent.

22. The absorbent article of claim 20, wherein the cover entirely encloses the absorbent.

23. The absorbent article of claim 18, wherein the absorbent further comprises a superabsorbent polymer.

24. An absorbent article (40) comprising an absorbent (66) and a fluid permeable cover (62), the absorbent article having a principal longitudinal axis and a principal transverse axis, and being configured to provide a labial pad for disposition within the vestibule of a female wearer, the absorbent having a maximum longitudinal length of no greater than about 100 mm extending from a first transverse end (76) to a spaced apart second transverse end (78), a body-facing surface of the absorbent having a minimum longitudinal length ($L_{min}$) that lies generally along said principal longitudinal axis from said first transverse end to said second transverse end and is less than said maximum longitudinal length, a maximum width of no greater than about 70 mm, a widest portion, a width at the widest portion, a narrowest portion, a width at the narrowest portion which is smaller than said width at the widest portion, a maximum thickness of no greater than about 10 mm, first (70) and second (72) end regions and a central region (74) disposed between the first and second end regions, and first (80) and second (82) spaced apart longitudinal sides, the longitudinal sides together with the transverse ends generally forming the periphery of the absorbent, wherein the widest portion of the absorbent is not situated in the central region, and the article is to be folded parallel to said longitudinal axis prior to disposition within the vestibule of the wearer.

25. The absorbent article of claim 24, wherein the widest portion of the absorbent is situated in the first end region.

26. The absorbent article of claim 25, wherein the narrowest portion of the absorbent is situated in said central region of the absorbent, a second widest portion of the absorbent is situated in the second end region of the absorbent, and said width of the narrowest portion is smaller than said width of the second widest portion.

27. The absorbent article of claim 24, wherein the widest portion of the absorbent is situated in the second end region.

28. The absorbent article of claim 24, wherein the cover has a periphery which is coterminous with the periphery of the absorbent.

29. The absorbent article of claim 28, further comprising a liquid impermeable baffle (64), the baffle having a periphery which is coterminous with the periphery of the absorbent.

30. The absorbent article of claim 24, further comprising a liquid impermeable baffle (64).

31. The absorbent article of claim 24, wherein the cover encloses the absorbent.

32. The absorbent article of claim 24, wherein the absorbent further comprises a superabsorbent polymer.

* * * * *